US007833724B2

(12) United States Patent
DiLiberti et al.

(10) Patent No.: US 7,833,724 B2
(45) Date of Patent: Nov. 16, 2010

(54) METHODS FOR COMPARING THE IMMUNOGENICITY OF PRODUCTS AND USES THEREOF

(75) Inventors: Charles E. DiLiberti, Montclair, NJ (US); Alan Liss, Gaithersburg, MD (US)

(73) Assignee: Teva Women's Health, Inc., Woodcliff Lake, NJ (US)

( * ) Notice: Subject to any disclaimer, the term of this patent is extended or adjusted under 35 U.S.C. 154(b) by 658 days.

(21) Appl. No.: 11/688,625

(22) Filed: Mar. 20, 2007

(65) Prior Publication Data

US 2007/0218517 A1 Sep. 20, 2007

Related U.S. Application Data

(60) Provisional application No. 60/783,407, filed on Mar. 20, 2006, now abandoned.

(51) Int. Cl.
*G01N 33/53* (2006.01)
(52) U.S. Cl. ....................................................... 435/7.1
(58) Field of Classification Search ........................ None
See application file for complete search history.

(56) References Cited

U.S. PATENT DOCUMENTS

| | | | |
|---|---|---|---|
| 5,135,874 A | 8/1992 | Esmon et al. | |
| 5,147,779 A | 9/1992 | Esmon et al. | |
| 5,470,560 A | 11/1995 | Martin, Jr. | |
| 5,639,440 A | 6/1997 | Martin, Jr. | |
| 5,667,988 A | 9/1997 | Barbas et al. | |
| 5,766,898 A * | 6/1998 | Loevborg | 510/392 |
| 6,045,501 A | 4/2000 | Elsayed et al. | |
| 6,300,064 B1 | 10/2001 | Knappik et al. | |
| 6,315,720 B1 | 11/2001 | Williams et al. | |
| 6,420,113 B1 | 7/2002 | Buechler et al. | |
| 6,555,310 B1 | 4/2003 | Gray et al. | |
| 6,561,976 B2 | 5/2003 | Elsayed et al. | |
| 6,561,977 B2 | 5/2003 | Williams et al. | |
| 6,673,580 B2 * | 1/2004 | Koren et al. | 435/91.4 |
| 6,686,164 B1 * | 2/2004 | Olsen et al. | 506/1 |
| 6,755,784 B2 | 6/2004 | Williams et al. | |
| 2002/0160358 A1 | 10/2002 | Schenerman et al. | |
| 2003/0054424 A1 | 3/2003 | Allen et al. | |
| 2004/0175757 A1 | 9/2004 | Olsen et al. | |
| 2004/0212508 A1 | 10/2004 | Zweig | |
| 2005/0191692 A1 | 9/2005 | Thompson et al. | |

OTHER PUBLICATIONS

Chamberlain, P., "Immunogenicity of therapeutic proteins: Part 1: Causes and clinical manifestations of immunogenicity," *The Regulatory Review* 5:4-9, Ministry of Economic Development's Effective Markets Branch (2002).
Coan, T.D. and Ellis, R., "Generic Biologics: The Next Frontier," in *ABN-AMRO*, Coan, T.D. and Ellis, R., eds., The Netherlands (2001).

Dempster, A.M., "Nonclinical safety evaluation of biotechnologically derived pharmaceuticals," *Biotechnol Annu Rev* 5:221-258, Elsevier Science B.V. (2000).
Esmon, P.C., et al., "Characterization of Recombinant Factor VIII and a Recombinant Factor VIII Deletion Mutant Using a Rabbit Immunogenicity Model System," *Blood* 76:1593-1600, American Society of Hematology (1990).
"Guidance for Industry: Immunotoxicology Evaluation of Investigational New Drugs," U.S. Department of Health and Human Services, Food and Drug Administration, Center for Drug Evaluation and Research (CDER), 35 pages (2002).
Halder, M., "Three Rs Potential in the Development and Quality Control of Immunobiologicals," *Altex* 18:13-47, Spektrum Akademischer Verlag (2001).
Hellendoorn, K., et al., "Limiting the risk of immunogenicity by identification and removal of T-cell epitopes (DeImmunisation™)" *Cancer Cell International* 4:S20, BioMed Central Ltd (2004).
Ji, Q.C., et al., "Investigation of the Immunogenicity of a Protein Drug Using Equilibrium Dialysis and Liquid Chromatography Tandem Mass Spectrometry Detection," *Anal. Chem.* 77:5529-5533, American Chemical Society (Sep. 2005).
Mintz, P.J., et al., "Fingerprinting the circulating repertoire of antibodies from cancer patients," *Nature Biotechnology* 21:57-63, Nature Publishing Group (2002).
Mire-Sluis, A.R., et al., "Standardization: Recommendations for the design and optimization of immunoassays used in the detection of host antibodies against biotechnology products," *Journal of Immunological Methods* 289:1-16, Elsevier B.V. (2004).
Moxness, M., et al., "Immunogenicity Testing by Electrochemiluminescent Detection for Antibodies Directed against Therapeutic Human Monoclonal Antibodies," *Clinical Chemistry* 51:1983-1985, American Association for Clinical Chemistry (Oct. 2005).
Schellekens, H., "Bioequivalence and the Immunogenicity of Biopharmaceuticals," *Nat Rev Drug Discov* 1:457-462, Nature Publishing Group (2002).
Schellekens, H. and Ryff, J.-C., "'Biogenerics': the off-patent biotech products," *Trends in Pharmacological Sciences* 23:119-121, Elsevier Science Ltd. (2002).
(Transcripts) "Drug Information Association, FDA/DIA Scientific Workshop on Follow-on Protein Pharmaceuticals, Breakout Session E: Immunogenicity Studies," Marriott Crystal Gateway, Arlington, VA, 83 pages (Feb. 15, 2005).
Wadhwa, M., et al., "Strategies for detection, measurement and characterization of unwanted antibodies induced by therapeutic biologicals," *Journal of Immunological Methods* 278:1-17, Elsevier B.V. (2003).
International Search Report and Written Opinion for International Application No. PCT/US2007/006843, mailed on Nov. 27, 2007, United States Patent and Trademark Office, Alexandria, VA.

* cited by examiner

*Primary Examiner*—David A Saunders
(74) *Attorney, Agent, or Firm*—Sterne, Kessler, Goldstein & Fox P.L.L.C.

(57) ABSTRACT

The present invention relates to methods of determining the immunogenic potential of a test product by comparing the immunogenic profile or fingerprint of the test product to the immunogenic profile or fingerprint of a reference product.

23 Claims, No Drawings

METHODS FOR COMPARING THE IMMUNOGENICITY OF PRODUCTS AND USES THEREOF

This application claims the benefit of the filing date of U.S. Appl. No. 60/783,407, filed Mar. 20, 2006, the contents of which are hereby incorporated by reference in its entirety.

FIELD OF THE INVENTION

The present invention relates to methods of determining the immunogenic potential of a test product by comparing the immunogenic profile or fingerprint of the test product to the immunogenic profile or fingerprint of a reference product.

BACKGROUND ART

One of the principle obstacles to the development of generic equivalents to biological and/or biotechnology-derived products is the absence of a practical, non-clinical method to compare the immunogenic potential of a proposed generic product with the immunogenic potential of an approved brand name reference product.

The immunogenic potential of a product is primarily based upon the three-dimensional shape and surface properties of the various molecular species present within that product. Immunogenicity can be further influenced by biological interactions between one or more species of the product and one or more endogenous compounds in a subject ingesting the product. Therefore, products that share the identical amino acid sequence can have disparate immunogenic potentials due to the presence of distinct molecular species within each product or due to the immunogenic properties of distinct formulation components of each product. Thus, while two proteins can share identical amino acid sequences (primary structure), the distinct molecular species of the proteins can comprise multiple three-dimensional conformations with distinct immunogenic properties. These differences in the three-dimensional structures of protein products can lead to differences in the immunogenic potential of the two protein products that share an identical primary amino acid sequence. Additionally, many of the biological products currently available (including both naturally-derived and biotechnologically-derived products) are not pure homogenous compounds. Rather, the products are heterogeneous mixtures of closely related molecular species. Even the products that are "substantially" homogeneous often contain low levels of impurities, such as degradation products, that are closely related to the "primary" product. In either case, the heterogeneous mixture or the presence of low level of impurities can contribute to the immunogenic potential of a given product. Thus, analytical methods which attempt to quantify immunogenicity by comparing only the amino acid sequence of two protein-base products and not the multiple three-dimensional molecular structures of the heterogeneous mixture are incapable of detecting the immunogenicity of the product resulting from the conformational differences between the distinct molecular species present within that product. Thus, there is a need in the art for methods which are capable of determining the distinct immunogenic potential profiles of protein-based products which have different formulations or are manufactured by distinct processes.

Methods of determining the immunogenic potential of biotechnological products, as well as other proteinaceous products, have been described, i.e., animal models have been used to assess the immunogenic potential of products. One such method includes the repeated administration of the protein of interest and subsequent evaluation of the animal for clinical signs. This method is not particularly useful because it is expected that all peptides larger than 5 kD will elicit an immune response in a non-homologous species. Therefore, the presence of an immune response is to be expected in such a protocol. Additionally, the mere quantification of these antibodies is not particularly insightful, since comparisons among different peptides and different species are not particularly informative. A second method for determining immunogenicity of a peptide product involves the repeated administration of the "final" product and subsequent animal evaluation. Such evaluations include observation of the animal for anaphylactic reactions and the measurement of immune complexes in the immunized animal. However, such methods are considered to be an inadequate means of determining the safety of the product in humans because of the lack of a direct correlation between the immune response that can occur in an animal model and the immune response that can occur in a human when exposed to the same potentially immunogenic product. Thus, human clinical trials represent the current benchmark for evaluating the immunogenic potential of biologically-derived pharmaceutical products.

In such human clinical trials, a biologically-derived pharmaceutical product is administered to a patient group and the group is evaluated for adverse immunological responses. Such adverse immunological responses include anaphylaxis, as well as the development of autoimmunity toward both the biologically-derived pharmaceutical product and the equivalent endogenous compound. For example, if a pharmaceutical preparation comprising recombinant DNA-produced insulin was administered to a human patient group and one of the patients were to develop anti-insulin antibodies in response to the recombinant protein, such anti-insulin antibodies could bind and inactivate any circulating insulin in that patient, including endogenously produced insulin. As a result, it would be very difficult to maintain adequate levels of insulin in said patient, even with the exogenous administration of insulin. Thus, human clinical trials which evaluate the immunogenicity of biotechnologically-derived pharmaceutical products can expose patient groups to an unnecessarily high degree of risk. Moreover, conducting human clinical trials is both time consuming and prohibitively costly. Further, the trials often provide spurious or variable results. Additionally, in the case of developing a generic equivalent to a brand-name biotechnologically-derived product, such human trials may preclude the filing of an abbreviate new drug application (ANDA), under section 505(j)(2)(C) of the Federal Food, Drug and Cosmetic Act (FD&C Act), thereby precluding the possibility of an 180 day market exclusivity period for the generic product under the Hatch-Waxman Act.

Thus, there exists a need in the art for a precise, non-clinical method of comparing the immunogenic profile of a test product with the immunogenic profile of a known reference product to evaluate the safety and efficacy of the test product relative to the safety and efficacy of the reference product.

BRIEF SUMMARY OF THE INVENTION

The present invention is directed to a method of comparing an immunogenicity of a test product to an immunogenicity of a known reference product comprising: (a) administering the test product to a subject to produce antibodies to the test product; (b) contacting the antibodies of (a) with fragments of the test product to form antibody-fragment complexes; (c) contacting the antibody-fragments of (b) with the test product to displace the fragments from the antibody-fragment complexes; (d) contacting the antibody-fragment complexes of (b) with the reference product to displace the fragments from the antibody-fragment complexes; and (e) comparing the fragments displaced by the test product to the fragments displaced by the reference product.

The present invention is further directed to a method of comparing an immunogenicity of a test product to an immunogenicity of a known reference product comprising: (a) administering the reference product to a subject to produce antibodies to the reference product; (b) contacting the antibodies of (a) with fragments of the reference product to form reference antibody-fragment complexes; (c) contacting the reference antibody-fragments of (b) with the test product to displace the reference fragments from the reference antibody-fragment complexes; (d) contacting the reference antibody-fragment complexes of (b) with the reference product to displace the reference fragments from the reference antibody-fragment complexes; and (e) comparing the reference fragments displaced by the test product to the reference fragments displaced by the reference product. In some embodiments, this method can further comprise: (f) administering the test product to a subject to produce antibodies to the test product, wherein the subject is the same subject or a different subject; (g) contacting the antibodies of (f) with fragments of the test product to form test antibody-fragment complexes; (h) contacting the test antibody-fragment complexes of (g) with the test product to displace the test fragments from the test antibody-fragment complexes; (i) contacting the test antibody-fragment complexes of (g) with the reference product to displace the test fragments from the test antibody-fragment complexes; and (j) comparing the test fragments displaced by the test product to the test fragments displaced by the reference product.

The present invention is directed to a method of determining an effect of a change in a manufacturing process on an immunogenicity of a test product, wherein the test product and a reference product are produced using at least one differing manufacturing process, the method comprising: (a) administering the test product to a subject to produce antibodies to the test product; (b) contacting the antibodies with fragments of the test product to form antibody-fragment complexes; (c) contacting the antibody-fragment complexes of (b) with the test product to displace fragments from the antibody-fragment complexes; (d) contacting the antibody-fragment complexes of (b) with the reference product to displace fragments from the antibody-fragment complexes; and (e) comparing the fragments displaced by the test product to the fragments displaced by the reference product.

In some embodiments, the change in manufacturing process can be selected from the group consisting of a change in a manufacturing procedure, manufacturing site, manufacturing scale, manufacturing equipment, formulation, source of cells, type of cells, method of cell culture, reagent, purification technique, and combinations thereof.

The present invention is also directed to an in vitro method of comparing an immunogenicity of a test product to an immunogenicity of a reference product comprising: (a) generating fragments of the test product; (b) contacting the fragments of (a) with antibodies generated from an antibody library to form antibody-fragment complexes; (c) contacting the antibody-fragment complexes of (b) with the test product to displace the fragments from the antibody-fragment complexes; (d) contacting the antibody-fragment complexes of (b) with the reference product to displace the fragments from the antibody-fragment complexes; and (e) comparing the fragments displaced by the test product to the fragments displaced by the reference product.

The antibodies generated from an antibody library can be a representation of the immunological repertoire of an animal. In some embodiments, the antibodies generated from an antibody library are from a human antibody library.

The methods of the present invention can further comprise repeated administration of the test product to the test subject.

The methods of the present invention can further comprise co-administration of an adjuvant with the test product. In some embodiments of the present invention, the adjuvant is a humoral immune adjuvant such as Freund's complete adjuvant and Freund's incomplete adjuvant. In other embodiments, the adjuvant is a mucosal immune adjuvant such as cholera toxin, pertussin toxin, and heat-labile toxin.

The methods of the present invention can further comprise administration of the test product to an animal. In some embodiments, the animal can be selected from the group consisting of mice, rats, rabbits, hamsters, guinea pigs, cats, dogs, pigs, goats, sheep, cows, monkeys, and apes.

The methods of the present invention can further comprise purification of the antibodies produced according to the methods of the present invention.

The methods of the present invention can further comprise partial hydrolysis of the test product into fragments. In some embodiments, the partial hydrolysis of the test product is performed using a protease.

In some embodiments of the present invention, the fragments of the test product can be peptides.

In some embodiments, the fragments of the antibody-fragment complexes can be displaced by a portion of an intact immunogenic species in the test product or reference product.

The methods of the present invention can further comprise analysis of the displaced fragments of the present invention using techniques selected from the group consisting of electrophoresis, isoelectric focusing, mass spectrometry, nuclear magnetic resonance, liquid chromatography, and combinations thereof.

The methods of the present invention can further comprise labeling the peptide fragments produced by the methods of the present invention with a detectable agent.

The methods of the present invention can further comprise repeating the methods of the present invention using a different test subject.

The methods of the present invention can further comprise repeating the methods of the present invention using fragments resulting from a different method of hydrolysis of the test product. In some embodiments, a different protease can be used in the hydrolysis of the test product.

The test product can be selected from the group consisting of proteinaceous pharmaceutical products, recombinant DNA products, peptides, and products derived from naturally occurring proteins.

DETAILED DESCRIPTION OF THE INVENTION

The present invention is directed to a method of comparing an immunogenicity of a test product to an immunogenicity of a known reference product comprising: (a) administering the test product to a subject to produce antibodies to the test product; (b) contacting the antibodies of (a) with fragments of the test product to form antibody-fragment complexes; (c) contacting the antibody-fragments of (b) with the test product to displace the fragments from the antibody-fragment complexes; (d) contacting the antibody-fragment complexes of (b) with the reference product to displace the fragments from the antibody-fragment complexes; and (e) comparing the fragments displaced by the test product to the fragments displaced by the reference product.

The present invention is also directed to a method of comparing an immunogenicity of a test product to an immunogenicity of a known reference product comprising: (a) administering the reference product to a subject to produce antibodies to the test product; (b) contacting the antibodies of (a) with fragments of the reference product to form antibody-fragment complexes; (c) contacting the antibody-fragments of (b) with the test product to displace the reference fragments from the reference antibody-fragment complexes; (d) contacting the reference antibody-fragment complexes of (b) with the reference product to displace the reference fragments from the reference antibody-fragment complexes; and (e) comparing the reference fragments displaced by the test product to the reference fragments displaced by the reference product. This method can further comprise: (f) administering the test product to a subject to produce antibodies to the test product, wherein the subject is the same subject or a different subject; (g) contacting the antibodies of (f) with fragments of the test product to form test antibody-fragment complexes; (h) contacting the test antibody-fragment complexes of (g) with the test product to displace the test fragments from the test antibody-fragment complexes; (i) contacting the test antibody-fragment complexes of (g) with the reference product to displace the test fragments from the test antibody-fragment complexes; and j) comparing the test fragments displaced by the test product to the test fragments displaced by the reference product.

The present invention is further directed to a method of determining an effect of a change in a manufacturing process on an immunogenicity of a test product comprising comparing the immunogenicity of the test product to immunogenicity of a reference product, wherein the test product and the reference product are produced using at least one differing manufacturing process, the method comprising: (a) administering the test product to a subject to produce antibodies to the test product; (b) contacting the antibodies of (a) with fragments of the test product to form antibody-fragment complexes; (c) contacting the antibody-fragment complexes of (b) with the test product to displace fragments from the antibody-fragment complexes; (d) contacting the antibody-fragment complexes of (b) with the reference product to displace fragments from the antibody-fragment complexes; and (e) comparing the fragments displaced by the test product to the fragments displaced by the reference product.

The present invention is also directed to an in vitro method of comparing an immunogenicity of a test product to an immunogenicity of a reference product comprising: (a) generating fragments of the test product; (b) contacting the fragments with antibodies generated from an antibody library to form antibody-fragment complexes; (c) contacting the antibody-fragment complexes of (b) with the test product to displace the fragments from the antibody-fragment complexes; (d) contacting the antibody-fragment complexes of (b) with the reference product to displace the fragments from the antibody-fragment complexes; and (e) comparing the fragments displaced by the test product to the fragments displaced by the reference product.

As used herein, "immunogenicity" refers to a product's ability to evoke an immune response within a subject. Immunogenicity depends upon the size and molecular conformation of the product in question and upon how different the product is from molecular species found endogenously in the recipient subject.

As used herein, the phrase "test product" refers to any known material, compound, or formulation for which immunogenicity can be evaluated. In some embodiments, test products can include active pharmaceutical agents, either alone or in combination with a suitable pharmaceutical formulation, including, but not limited to, pharmaceutical products intended for human and/or veterinarian use. Additionally, test products can include products such as, but not limited to, genetically engineered food and agricultural products. In some aspects of the invention, the test product comprises active agents that are produced by methods known in the art of medicinal chemistry, such as organic molecule synthesis or high-throughput compound screening. In other aspects of the invention, the test product comprises an active agent that is produced from biotechnological methods, including but not limited to, recombinant DNA-engineering, polyclonal and monoclonal antibody production methods, and transgenic animal technologies. Thus, a test product includes, but is not limited to, proteinaceous pharmaceutical products, recombinant DNA products, peptides, and products derived from naturally occurring proteins. Further, a test product can include both the active agent together with a suitable formulation, as well as the native and/or formulated active agent in the presence of human substances such as human serum, human serum albumin, or other such components. Additionally, a test product includes an active agent alone or together with a suitable formulation further in the presence of gastric juices or similar substances. "Pharmaceutical," as used herein, refers to those compounds, materials, compositions, and/or dosage forms which are, within the scope of sound medical judgment, suitable for contact with the tissues of human beings and animals without excessive toxicity, irritation, allergic response, and other complications commensurate with a reasonable risk/benefit ratio.

"Reference product," as used herein, refers to any known material, compound, or formulation used as the reference standard in an immunogenic comparison between two or more materials, compounds, or formulations. In some aspects of the invention, the reference product can be a brand name pharmaceutical product, which may or may not be federally approved. In other aspects, the reference product can be a material, compound, or formulation produced in a specific production cycle which has passed certain production specifications, e.g., for use in determining batch to batch consistency for quality control. In such embodiments, the reference product acts as a standard by other which materials, compounds, or formulations produced in separate, distinct production cycles are compared in order to determine whether the products of the separate, distinct production cycles meet internal manufacturing specifications. In other aspects, the reference product can be a natural or genetically engineered agricultural or food product. In still other aspects of the invention, the reference product can comprise active agents that are produced by methods known in the art of medicinal chemistry, such as organic molecule synthesis or high-throughput compound screening. In yet other aspects of the invention, the reference product can comprise an active agent that is produced from biotechnological methods, including but not limited to, recombinant DNA-engineering, polyclonal and monoclonal antibody production methods, and transgenic animal technologies. Further, reference products can include both the active agent together with its appropriate formulation, as well as the native and/or formulated active agent in the presence of human substances such as human serum, human serum albumin, or other such components. Additionally, "reference product" can include the active agent alone or together with its appropriate formulation further in the presence of gastric juices or similar substances.

In some aspects of the present invention, an adjuvant can be co-administered with the test and/or reference product. An adjuvant is any substance which enhances the immune-stimulating properties of an antigen or the pharmacological effect of a drug. As used herein, adjuvant includes, but is not limited to, humoral immune adjuvants and mucosal immune adjuvants. Examples of humoral immune adjuvants include, but are not limited to, Freund's complete adjuvant, Freund's incomplete adjuvant and alum. Examples of mucosal immune adjuvants include, but are not limited to, cholera toxin, pertussin toxin and heat-labile toxin.

"Administering," as used herein, refers to the dispensing of a test and/or reference product to a test subject. Routes of administration include, but are not limited to, oral, percutaneous, subcutaneous, intramuscular, and intravenous.

"Subject," as used herein, refers to any species, including human and animal species, in which a suitable immune response can be generated and analyzed according to the methods of the present invention. The subjects will typically be from an animal species, such as, but not limited to, non-human mammalian species. In certain embodiments, the subjects are selected from the group consisting of mice, rats, rabbits, hamsters, guinea pigs, cats, dogs, pigs, goats, sheep, cows, monkeys and apes. In addition, the subjects can be birds, such as chickens. In some embodiments, the methods of the invention include using different individual subjects and/or different species of subjects to enhance the likelihood of detecting subtle differences between the immunogenic potential of the test product and reference product.

"Antibodies," as used herein, refer to immunoglobulin molecules comprising an immunoglobulin heavy chain component and/or an immunoglobulin light chain component which recognize a particular epitope on a potentially immunogenic molecule. A typical immune response yields a heterogeneous mixture of polyclonal antibodies representative of the relative immunogenicity of the substance used to generate the immune response. Thus, the number and types of immunoglobulin molecules generated in response to the administration of the substance is indicative of the immunogenic potential of the administered substance. In such a polyclonal immune response, the immunoglobulin molecules can be of any type (e.g., IgG, IgE, IgM, IgD, IgA and IgY), class (e.g., IgG1, IgG2, IgG3, IgG4, IgA1 and IgA2) or subclass of immunoglobulin molecule. For example, an immune response to a substance represented by the generation of a large number of antibodies of the various types, classes and subclasses of immunoglobulin molecules is indication that the administered substance is highly immunogenic. In some embodiments of the present invention, polyclonal antibody preparations can be used according to the methods describe herein. In other embodiments, monoclonal antibodies can be used according to the methods describe herein.

In addition to antibodies produced by the in vivo humoral immune response of an immunized subject, it is to be understood that antibodies also include those immunoglobulin molecules generated from an antibody library. "Antibody libraries," as used herein, refer to collections of genes that encode immunoglobulin molecules, i.e., antibodies. Antibody libraries enable one to generate a fall repertoire of antibodies precisely tailored to a intended antigen. Methods for generating such antibody libraries are known in the art and are discussed in, e.g., Winter et al., *Annu. Rev. Immuno.* 12:433-55 (1994), Chester et al., *Lancet* 343:455-6 (1994), U.S. Pat. Nos. 5,667,988, 6,300,064, 6,420,113, and 6,555,310, all of which are fully incorporated by reference in their entirety. In some embodiments of the present invention, the antibodies are generated from antibody libraries.

In some embodiments of the present invention, a test product can be administered to a suitable subject with the intent of inducing polyclonal antibody formation in the subject specific for the test product. This can be accomplished by repeatedly administering the test product to the subject over the course of several weeks. In some aspects of the invention, antibody formation can be enhanced by co-administration of the test product with a suitable adjuvant, such as Freund's complete adjuvant. For example, the protein product of interest can be emulsified in an aqueous buffer with an equal volume of Freund's complete (for the first injection) or incomplete (for later injections) or the protein product can be co-precipitated with alum. The mixture of protein product and adjuvant can be injection subcutaneously or intramuscularly into the test subject. Although the injection schedule can vary, two injections at 2 week intervals is commonly used to test the immunogenicity of the protein. After a sufficient number of administrations, and a sufficient length of time, the test subject will develop antibodies to the various immunogenic materials in the test product. These methods are known in the art and are disclosed in, e.g., Harlow, E. and Lane, D., *Antibodies A Laboratory Manual*, Ch. 5 (Cold Spring Harbor Laboratory, N.Y. (1988)) and Harlow, E. and Lane, D., *Using Antibodies A Laboratory Manual*, (Cold Spring Harbor Laboratory, N.Y. (1998)). Polyclonal antibodies resulting from the methods describe herein are generally a heterogeneous mixture of the various types, classes and subclasses of immunoglobulin molecules which recognize and bind to various immunogenic portions of the various molecular species and conformers present in the test product.

Once the subject has been immunized with the test product and has generated an immune response to the test product, portions of the subject's blood serum can be collected and the antibodies directed to the different immunogenic portions of the test product can be isolated and purified. Antibodies can be isolated and purified using conventional methods known in the art such as column chromatography, e.g., antigen affinity column chromatography. Such methods are described in, e.g., Harlow, E. and Lane, D., *Antibodies A Laboratory Manual*, Ch. 8 (Cold Spring Harbor Laboratory, N.Y. (1988)) and Harlow, E. and Lane, D., *Using Antibodies A Laboratory Manual*, (Cold Spring Harbor Laboratory, N.Y. (1998))

In other aspects of the present invention, in vitro methods of comparing the immunogenicity of a test product to the immunogenicity of a reference product are used wherein antibodies generated from an antibody library are utilized in place of antibodies generated from an in vivo immunization of a subject with the test product. In such embodiments, the antibody library can be generated by any method known in the art and can represent the full immunological repertoire of an animal species. In some embodiments, the antibody library can represent the fall immunological repertoire of a human.

The test product can be hydrolyzed in a manner that yields molecular fragments of sufficient size to compete with antibody-antigen interactions. In some embodiments of the present invention, one or more proteases, such as but not limited to endoproteases, can be used to partially hydrolyze the protein portion of the test product into distinct peptide fragments. Such partial proteolytic digestion methods are well known in the art and have been utilized in peptide mapping and epitope mapping. See *Current Protocols in Protein Science*, Unit 7.3 (editorial board, Coligan, J. E., et al., John Wiley & Sons, Inc., USA (2002)) and Mazzoni, M. R., et al., *Methods in Molecular Biology, Epitope Mapping Protocols* 66:109-120 (Morris, G. E., ed., Humana Press, Inc., Totowa, N.J. (1996)), both of which are fully incorporated by reference in their entirety. In some embodiments, a test product can be fragmented using multiple, independent protease digestions to generate an immunogenic profile or fingerprint of the test product. In such embodiments, the test product can be digested with multiple, specific proteases in independent reactions to form multiple fragment patterns of the test product. These individual patterns can be analyzed to generate multiple immunogenic profiles of the test product. Such multiple immunogenic profiles can provide additional data with which to determine the relative immunogenicity of a test product as compared to a reference product.

In some aspects of the invention, the fragments generated from the protease digestion can be labeled with a detectable agent. Examples of detectable agents include various enzymes, prosthetic groups, fluorescent materials, luminescent materials, bioluminescent materials, radioactive materials, and non-radioactive paramagnetic metal ions. The detectable agent can be coupled or conjugated either directly to the fragment or indirectly, through an intermediate such as, for example, a linker using techniques known in the art.

As used herein, the term "antibody-fragment complex" refers to a molecular structure formed when an antibody binds to a fragment. In such a complex, the bound fragment represents a potential immunogenic region present in the intact, unhydrolyzed protein.

Upon fragmenting the test product, the resultant mixture of test product fragments can then be mixed with antibodies to produce antibody-fragment complexes. Such procedures are well known in the art and are used, for example, in epitope mapping, wherein a variety of peptide fragments are used to assess the specificity of immunoglobulin species. In some embodiments, the antibodies of the invention can be bound to the surface of solid substrates such as ELISA plates or column beads for analysis of the antibodies' interactions with the fragments using assays such as competitive ELISAs and flow-through affinity columns. These techniques can be further combined with other immunoadsorption column chromatography methods in series with HPLC or similar separation technologies, i.e., MS/GC and MALDI-TOF.

The antibody-fragment complexes can be further exposed to the test product with the intent that any intact immunogenic species within the test product that binds to one of the test product induced antibodies can displace a particular fragment from the antibody-fragment complex, thereby releasing the previously bound fragment. In some aspects of the present invention, the fragment bound to the particular species of antibody are displaced by the portion of the intact immunogenic species present in the test product with similar shape and surface characteristics of the fragment that was displaced. The displaced fragments are then collected and analyzed such that the collection of displaced fragments is a direct reflection of the immunogenic surfaces of the various molecular immunogenic species present in the test product The displaced fragments can be collected and analyzed quantitatively or qualitatively by established methods including, but not limited to, electrophoresis, isoelectric focusing, mass spectrometry, nuclear magnetic resonance, liquid chromatography, liquid chromatography with mass spectrometric detection (LCMS), and combinations thereof to yield an immunogenic profile for the test product. In some aspects of the present invention, the displaced fragments can be labeled to facilitate detection and analysis. In such embodiments, the labeled fragments which are displaced by the test product can be analyzed using X-ray radiographic techniques or similar techniques utilized in the detection of labeled protein fragments. In some aspects of the invention, the immunogenic profile of the test product generated by the method described herein is compared with the immunogenic profile of a known reference product.

The antibody-fragment complexes formed from interactions with a partially hydrolyzed test product are likewise used to generate an immunogenic profile of the reference product. Thus, the antibody-fragment complexes can be used to probe the reference product in a manner analogous to the antibody-fragment complexes used to probe the test product.

Thus, the antibody-fragment complexes described supra are mixed with the specific reference product of interest. The immunogenic species of the reference product that have similar shape and surface characteristics as the immunogenic fragment bound to the antibody can be displaced by the immunogenic fragment from the antibody-fragment complex. The collection of displaced molecular fragments is directly reflective of the immunogenic surfaces of the molecular species present in the reference product. The collection of molecular fragments can then be analyzed quantitatively or qualitatively by established methods including, but not limited to, electrophoresis, isoelectric focusing, mass spectrometry, nuclear magnetic resonance, liquid chromatography, and combination thereof to yield an immunogenic profile of the reference product. In some aspects of the present invention, the fragments can be labeled to facilitate detection and analysis. In such embodiments, the labeled fragments which are displaced be the reference product can be analyzed using X-ray radiographic techniques or similar techniques utilized in the detection of chemi-luminescently labeled protein fragments.

The immunogenic profile of the test product can then be compared with the immunogenic profile of the reference product to determine the relative immunogenicity of the test product to that of the reference product. Such a comparison represents a direct measure of the relative immunogenic potential of the test and reference products. In some aspects of the invention, mathematical algorithms can be utilized to compare the immunogenic profiles of the test and reference products. In other embodiments, the comparison can be extended to include multi-way comparisons of immunogenic profiles of more than two distinct products.

One of the advantages of the methods of the present invention is that this method specifically stimulates the production of antibodies against the immunogenic molecular species present in the test product, rather than relying on the spontaneous formation of antibodies to the test product as is done in human clinical studies. The value in relying on the test product to immunize the test subjects and its use as the substrate for generating molecular fragments for the production of antibody-fragment complexes, is that the immunogenic potential of the test product is fully and thoroughly probed. If the reference product were used to immunize the subjects and to generate the antibody-fragment complexes, the potential exists for missing immunogenic species present in the test product but absent in the reference product. Thus, the method of the present invention, when using the test product both to immunize the test subjects and as the substrate for proteolytic fragmentation, provides a means of ensuring that the test product is not more immunogenic than the reference product. However, in some embodiments of the present invention, the reference product can be used to immunize the test subjects and as the substrate for proteolytic fragmentation, if a need exists to determine if the reference product is no more immunogenic that the test product.

In other embodiments, the reference product can be used to immunize the test subjects as described above, wherein these embodiments further comprise the administration of the test product to a previously immunized subject. Upon the immunization with the test product, antibodies from the test subject are isolated and purified. These antibodies are contacted with fragments of the test product to form antibody-fragment complexes. These antibody-fragment complexes are used to generate an immunogenic profile for both the test product and reference product as described above. The resulting immunogenic profiles are then compared to determine the relative immunogenicity of the test product to that of the reference product.

In another aspects of the invention, immunogenic equivalence can be determined by conducting experiments using either the test product or the reference product, respectively, as the immunizing agent and substrate for proteolytic fragmentation. The immunogenic profiles generated by these methods allow for the determination of immunogenic equivalence between the two products.

In other aspects of the present invention, the methods described herein provide a means by which an abbreviated new drug application (ANDA) can be submitted for a generic product that would otherwise need to undergo human clinical trials to assess safety. Pursuant to Federal Drug Administration (FDA) regulations, if a drug application requires human clinical trials to assess safety, it may not be submitted as an ANDA under section 505(j)(2)(C) of the Federal Food, Drug and Cosmetic Act (FD&C Act), and is therefore not eligible for 180-day generic market exclusivity. Thus, the present invention provides a means, via non-clinical studies, to avoid the use of human safety studies and still provide the FDA with adequate assurance that the generic test product is no more immunogenic than the approved brand name reference product.

In yet other aspects of the present invention, the methods of the present invention can be used to determine whether a change in manufacturing process, manufacturing site, purification method, master cell bank, working cell bank, or any other change in the manufacture of a biotechnological or natural product has any effect of the immunogenicity of the final product. In some embodiments the change in manufacturing process can be a change in manufacturing procedure, manufacturing site, manufacturing scale, manufacturing equipment, formulation, source of cells, type of cells, method of cell culture, reagent, purification technique, or combinations thereof. Thus, this method can be used to evaluate and justify such manufacturing changes without having to conduct any human clinical trials. In such embodiments, the test product is represented by the product manufactured via the altered manufacturing process and the reference product is represented by the product manufactured by the previously used method.

In some aspects of the present invention, the methods of the present invention can be used to determine whether a genetically engineered food or agricultural product has a distinct immunogenic profile as compared to the naturally occurring food or agricultural product. Thus, this method can be used to evaluate the potential immunogenicity of genetically modified food and agricultural product without having to conduct human clinical trials to access the safety of such genetically modified products. In such embodiments, the test product is represented by the genetically modified product and the reference product is represented by the naturally occurring, unmodified product.

The present invention is also directed to kits useful in the methods of the present invention. The kits can comprise one or more compartments or containers for holding the various materials used in the methods of the present invention. In some embodiments, the invention is directed to a kit comprising one or more reference products, optionally one or more proteases, optionally one or more detectable agents, optionally one or more adjuvants, optionally one or more suitable buffers, and optionally instructions for practicing a method of the present invention.

Having generally described the invention, a further understanding can be obtained by reference to the examples provided herein. These examples are for purposes of illustration only and are not intended to be limiting.

While specific configurations and arrangements are discussed, it should be understood that this is done for illustrative purposes only. A person skilled in the pertinent art will recognize that other configurations and arrangements can be used without departing from the spirit and scope of the present invention. It will be apparent to a person skilled in the pertinent art that this invention can also be employed in a variety of other applications.

While various embodiments of the present invention have been described above, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the following claims and their equivalents.

All documents recited herein (i.e., all scientific publications, patents and patent publications) are hereby incorporated by reference in their entirety to the same extent as if each individual document was specifically and individually indicated to be incorporated by reference in its entirety. Where the document cited only provides the first page of the document, incorporation of the entire document is intended, including the remaining pages of the document.

What is claimed is:

1. A method of comparing an immunogenicity of a test product to an immunogenicity of a reference product, the method comprising:
   a) administering the test product to a subject to produce antibodies to the test product;
   b) contacting the antibodies of (a) with fragments of the test product to form antibody-fragment complexes;
   c) contacting a first portion of the antibody-fragment complexes of (b) with the test product to displace the fragments from the antibody-fragment complexes;
   d) contacting a second portion of the antibody-fragment complexes of (b) with the reference product to displace the fragments from the antibody-fragment complexes; and
   e) comparing the fragments displaced by the test product to the fragments displaced by the reference product.

2. The method of claim 1, wherein (a) comprises repeatedly administering the test product to the subject.

3. The method of claim 1, wherein (a) further comprises administering an adjuvant with the test product.

4. The method of claim 3, wherein the adjuvant is a humoral immune adjuvant.

5. The method of claim 4, wherein the humoral immune adjuvant is selected from the group consisting of Freund's complete adjuvant and Freund's incomplete adjuvant.

6. The method of claim 3, wherein the adjuvant is a mucosal immune adjuvant.

7. The method of claim 6, wherein the mucosal immune adjuvant is selected from the group consisting of cholera toxin, pertussin toxin, and heat-labile toxin.

8. The method of claim 1, wherein the subject is an animal selected from the group consisting of mice, rats, rabbits, hamsters, guinea pigs, cats, dogs, pigs, goats, sheep, cows, monkeys and apes.

9. The method of claim 1, wherein the antibodies produced in (a) are purified.

10. The method of claim 1, wherein the fragments in (b) are obtained by partial hydrolysis of the test product.

11. The method of claim 10, wherein the partial hydrolysis of the test product is performed using a protease.

12. The method of claim 1, wherein the fragments of (b) are labeled with a detectable agent.

13. The method of claim 1, wherein the fragments are displaced by a portion of an intact immunogenic species in the test product or reference product.

14. The method of claim 1, wherein (e) comprises analyzing the fragments displaced using a technique selected from the group consisting of electrophoresis, isoelectric focusing, mass spectrometry, nuclear magnetic resonance, liquid chromatography, and combinations thereof.

15. The method of claim 1, further comprising repeating (a)-(e) using a different subject.

16. The method of claim 10, further comprising repeating (a)-(e) using fragments resulting from a different method of hydrolysis of the test product.

17. The method of claim 16, wherein a different protease is used in the hydrolysis of the test product.

18. The method of claim 1, wherein the test product is selected from the group consisting of proteinaceous products, recombinant DNA products, peptides, and products derived from naturally occurring proteins.

19. The method of claim 1, wherein the fragments of (b) are peptides.

20. A method of comparing an immunogenicity of a test product to an immunogenicity of a reference product, the method comprising:
    a) administering the reference product to a subject to produce antibodies to the reference product;
    b) contacting the antibodies of (a) with reference fragments of the reference product to foil reference antibody-fragment complexes;
    c) contacting a first portion of the reference antibody-fragment complexes of (b) with the test product to displace the reference fragments from the reference antibody-fragment complexes;
    d) contacting a second portion of the reference antibody-fragment complexes of (b) with the reference product to displace the reference fragments from the reference antibody-fragment complexes; and
    e) comparing the reference fragments displaced by the test product to the reference fragments displaced by the reference product.

21. The method of claim 20, further comprising:
    f) administering the test product to a subject to produce antibodies to the test product, wherein the subject is the same subject in (a) or a different subject;
    g) contacting the antibodies of (f) with test fragments of the test product to form test antibody-fragment complexes;
    h) contacting a first portion of the test antibody-fragment complexes of (g) with the test product to displace the test fragments from the test antibody-fragment complexes;
    i) contacting a second portion of the test antibody-fragment complexes of (g) with the reference product to displace the test fragments from the test antibody-fragment complexes; and
    j) comparing the test fragments displaced by the test product to the test fragments displaced by the reference product.

22. A method of determining an effect of a change in manufacturing process on an immunogenicity of a test product, the method comprising comparing the immunogenicity of the test product to the immunogenicity of a reference product, wherein the test product and the reference product are produced using at least one differing manufacturing process, the method comprising:
    a) administering the test product to a subject to produce antibodies to the test product;
    b) contacting the antibodies with fragments of the test product to form antibody-fragment complexes;
    c) contacting a first portion of the antibody-fragment complexes of (b) with the test product to displace fragments from the antibody-fragment complexes;
    d) contacting a second portion of the antibody-fragment complexes of (b) with the reference product to displace fragments from the antibody-fragment complexes; and
    e) comparing the fragments displaced by the test product to the fragments displaced by the reference product.

23. The method of claim 22, wherein the change in manufacturing process is selected from a change in the group consisting of a manufacturing procedure, manufacturing site, manufacturing scale, manufacturing equipment, formulation, source of cells used to produce the test product, type of cells used to produce the test product, method of cell culture, reagent used in the production of the test product, purification technique, and combinations thereof.

* * * * *